US011346784B2

(12) United States Patent
Takahashi et al.

(10) Patent No.: US 11,346,784 B2
(45) Date of Patent: May 31, 2022

(54) MEDIUM FOR RESIN PARTICLES CONTAINING FLUORESCENT DYE

(71) Applicant: KONICA MINOLTA, INC., Chiyoda-ku (JP)

(72) Inventors: Masaru Takahashi, Kokubunji (JP); Fuminori Okada, Taito-ku (JP)

(73) Assignee: KONICA MINOLTA, INC., Tokyo (JP)

( * ) Notice: Subject to any disclaimer, the term of this patent is extended or adjusted under 35 U.S.C. 154(b) by 309 days.

(21) Appl. No.: 16/561,732

(22) Filed: Sep. 5, 2019

(65) Prior Publication Data

US 2020/0003690 A1 Jan. 2, 2020

Related U.S. Application Data

(63) Continuation of application No. 15/305,416, filed as application No. PCT/JP2015/061567 on Apr. 15, 2015, now abandoned.

(30) Foreign Application Priority Data

Apr. 23, 2014 (JP) ................................ 2014-089287

(51) Int. Cl.

| | |
|---|---|
| ***C09K 11/06*** | (2006.01) |
| ***C09K 11/02*** | (2006.01) |
| ***G01N 21/64*** | (2006.01) |
| ***G01N 33/545*** | (2006.01) |

(Continued)

(52) U.S. Cl.

CPC ....... *G01N 21/6428* (2013.01); *C08K 5/3437* (2013.01); *C09K 11/025* (2013.01); (Continued)

(58) Field of Classification Search

CPC .............................. C09K 11/025; C09K 11/06

See application file for complete search history.

(56) References Cited

U.S. PATENT DOCUMENTS

| | | | |
|---|---|---|---|
| 5,262,299 | A | 11/1993 | Evangelista et al. |
| 5,326,692 | A | 7/1994 | Brinkley et al. |

(Continued)

FOREIGN PATENT DOCUMENTS

| | | |
|---|---|---|
| DE | 69017753 | 7/1995 |
| EP | 0581881 | 2/1994 |

(Continued)

OTHER PUBLICATIONS

Jin. Near-Infrared Fluorescent Dye-Doped Semiconducting Polymer Dots. ACS Nano vol 5. No. 2 1468-1475. 2011 (Year: 2011).*

(Continued)

*Primary Examiner* — Matthew E. Hoban

(74) *Attorney, Agent, or Firm* — Cozen O'Connor

(57) ABSTRACT

A method of storing fluorescent dye-containing resin particles comprising adding the fluorescent dye-containing resin particles in a liquid comprising a buffer, a protein, and a surfactant, thereby obtaining a particle-containing liquid. The rate of change in the backscatter intensity (transmitted light) at the center of the height of the particle-containing liquid left to stand for 24 hours after the adding is not less than −1% based on the particle-containing liquid immediately after the adding.

13 Claims, 4 Drawing Sheets

(51) Int. Cl.
*G01N 21/59* (2006.01)
*C08K 5/3437* (2006.01)

(52) U.S. Cl.
CPC .............. *C09K 11/06* (2013.01); *G01N 21/59* (2013.01); *G01N 21/64* (2013.01); *G01N 33/545* (2013.01); *C09K 2211/1416* (2013.01); *C09K 2211/1433* (2013.01); *G01N 2021/6439* (2013.01)

(56) References Cited

U.S. PATENT DOCUMENTS

| | | | |
|---|---|---|---|
| 5,338,659 A | 8/1994 | Kauvar et al. | |
| 2002/0187510 A1 | 12/2002 | Tachikawa et al. | |
| 2003/0124675 A1 | 7/2003 | Wallach et al. | |
| 2012/0122094 A1* | 5/2012 | May ..................... | G01N 33/533 435/6.11 |
| 2016/0178621 A1 | 6/2016 | Gouda et al. | |

FOREIGN PATENT DOCUMENTS

| | | |
|---|---|---|
| EP | 0596098 | 5/1994 |
| JP | 2013-503951 | 2/2013 |
| WO | WO 2012/029342 | 3/2012 |
| WO | WO 2013/147081 | 10/2013 |
| WO | WO 2014/203614 | 12/2014 |

OTHER PUBLICATIONS

Search Report dated Nov. 29, 2017 which issued in the corresponding European Patent Application No. 15783619.8.

Anonymous, "Drug Discovery Research Clinical Screening Assay Buffers for DELFIA," Jan. 1, 2002, Nov. 14, 2017, 2 pages.

Protocols/Recipes. AbC-arrays. http://www.abc-arrays.com/protocols.html-Retrieved on Aug. 11, 2018. Jun. 23, 2011 version of webpage retrieved from https://web/archive.org/web/20110623033126/http://www.abc-arrays.com/protocols.html (Year: 2011).

Fischer BioReagents. Prep of Tris: Preparation of Tris*CI Tri(hydroxymethyl)aminomethane Stock Soluations. Retrieved from https://www.fishersci.co.uk/webfiles/uk/web-docs/PAGE744.PDF on Apr. 8, 2019.

Final Office Action dated May 24, 2021 issued in U.S. Appl. No. 16/561,679.

Office Action dated Dec. 4, 2020 issued in U.S. Appl. No. 16/561,679.

* cited by examiner

[Fig. 1]
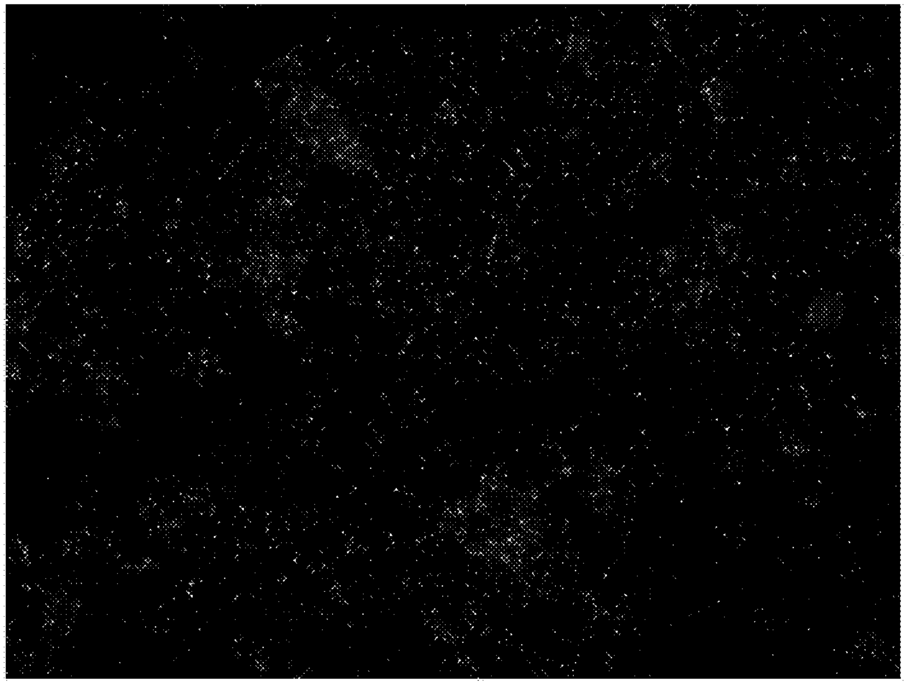
[Fig. 2]
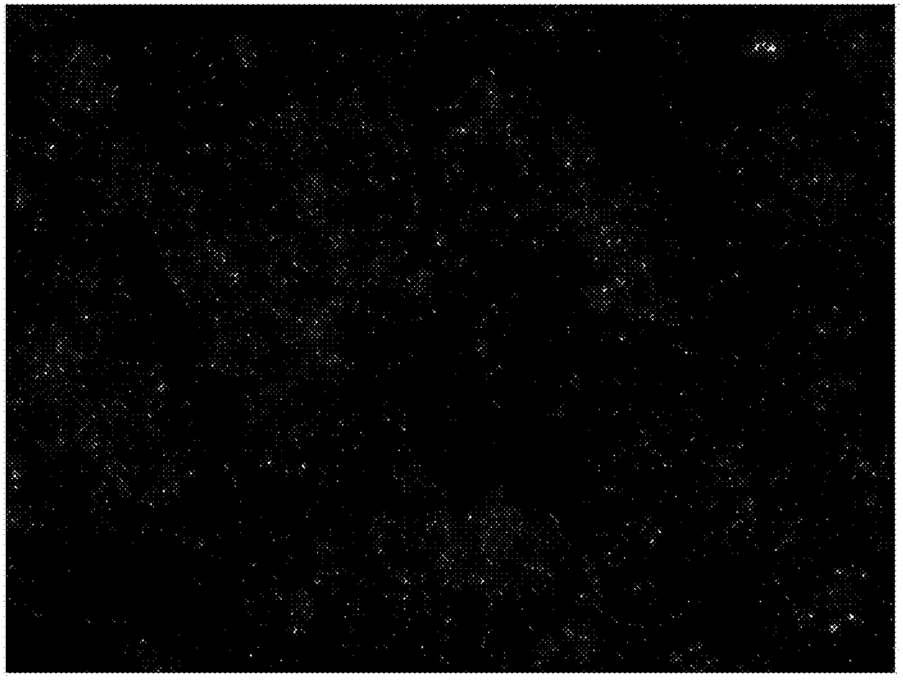

[Fig. 3]
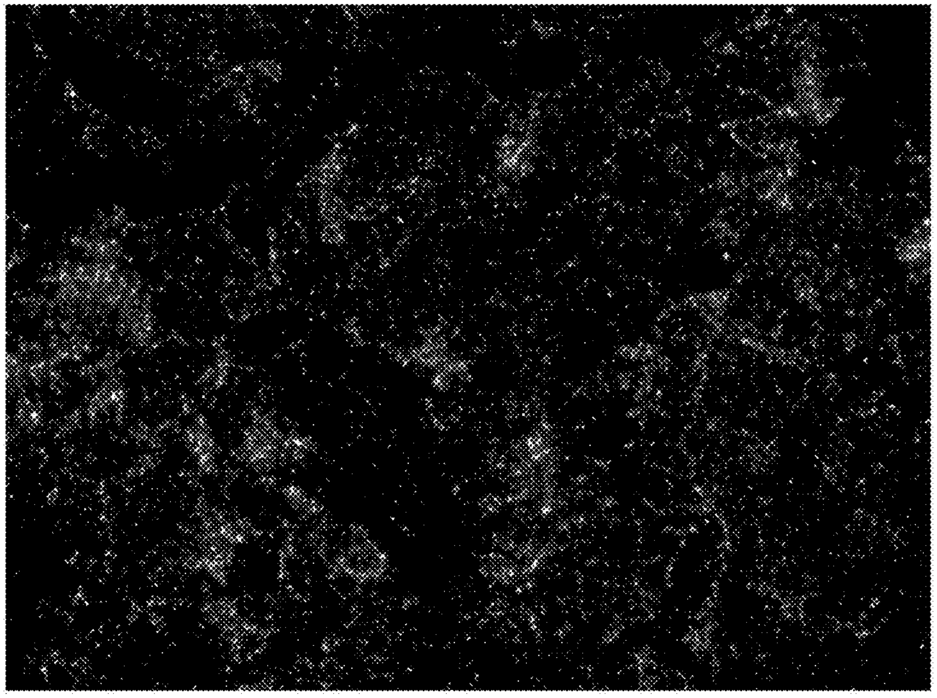
[Fig. 4]
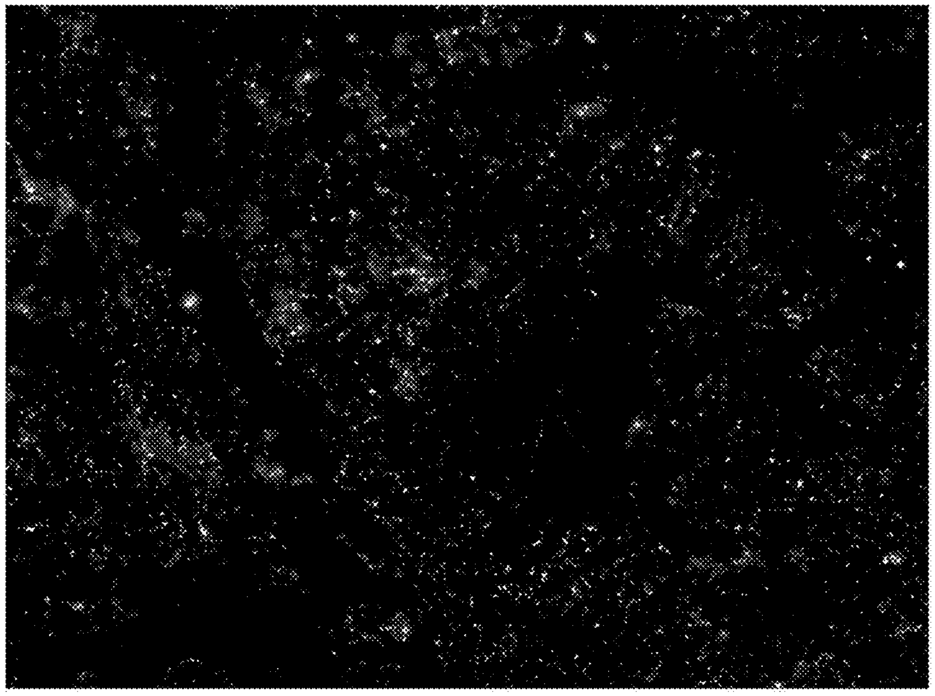

[Fig. 5]
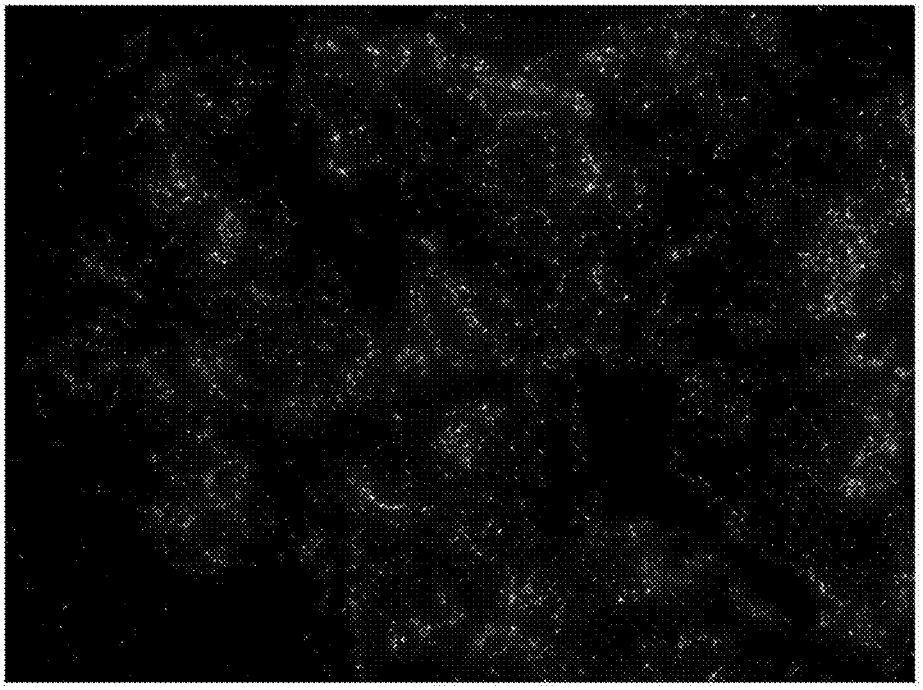
[Fig. 6A]
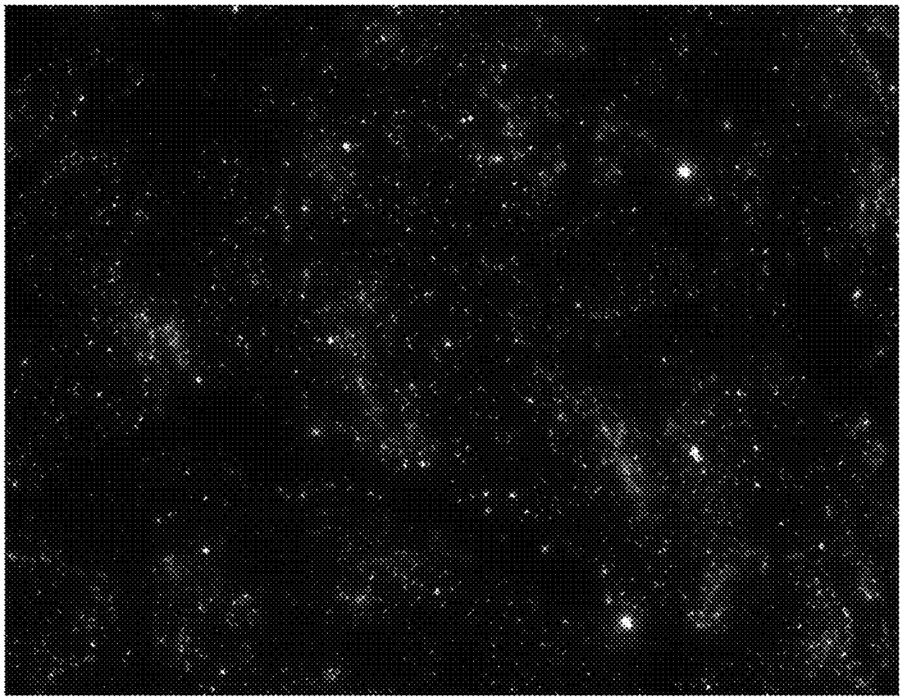

[Fig. 6B]
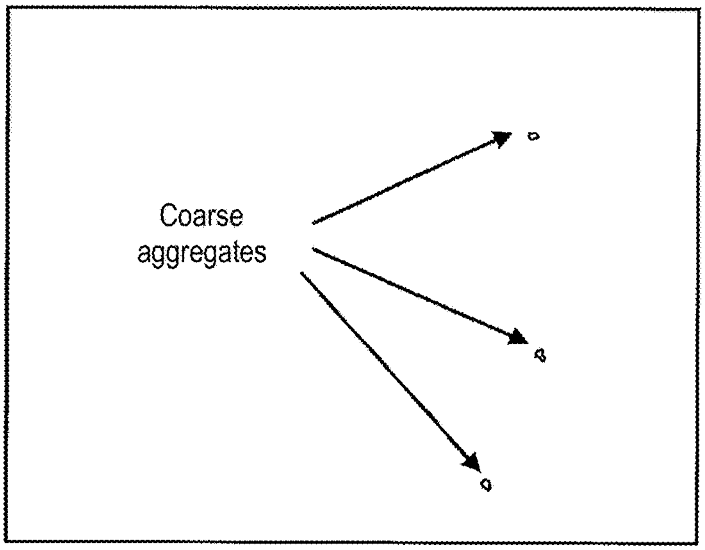
[Fig. 7]
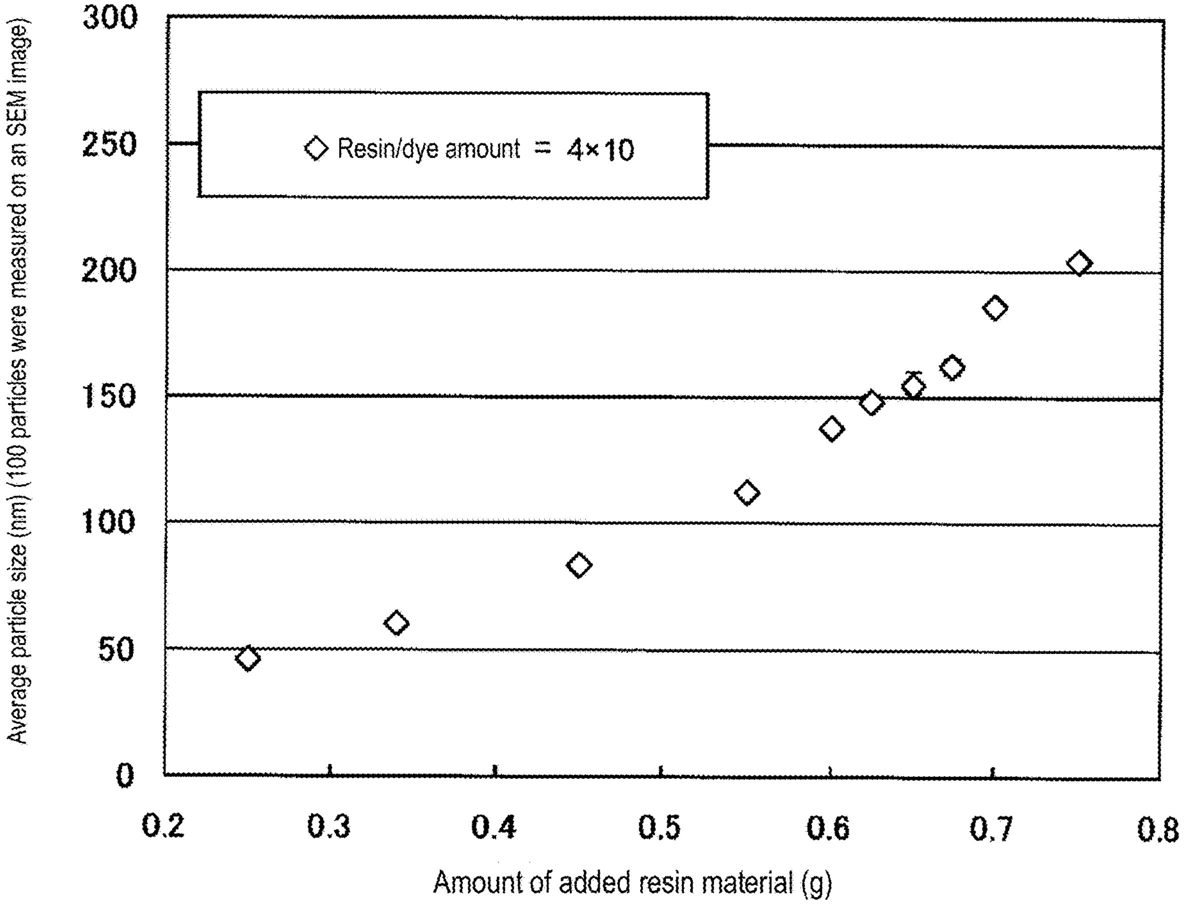

MEDIUM FOR RESIN PARTICLES CONTAINING FLUORESCENT DYE

RELATED APPLICATIONS

This application is a continuation of U.S. patent application Ser. No. 15/305,416 filed Oct. 20, 2016, which is a U.S. National Stage of International Application No. PCT/JP2015/061567 filed Apr. 15, 2015, which claims priority of Japanese application no. 2014-089287 filed Apr. 23, 2014, the entire content of all of which are hereby incorporated by reference.

TECHNICAL FIELD

The present invention relates to a medium used for storing fluorescent dye-containing resin particles.

BACKGROUND ART

In recent years, fluorescent dye-containing resin particles have begun to be used as fluorescent labels in the field of biology. Fluorescent dye-containing resin particles are particles having a structure in which a fluorescent dye is encapsulated by an appropriate resin particle. As fluorescent dye-containing resin particles, those in the form of a complex with a functional group or molecule that is capable of binding to a biological substance such as an antibody may also be used in applications such as immunostaining.

When such fluorescent dye-containing resin particles are used, they are not always used immediately after the production and may be stored for a certain period until use. In that case, the fluorescent dye-containing resin particles are often stored in a state of being diluted in a medium so that the functions as a fluorescent label can be maintained.

As a medium for storing fluorescent dye-containing resin particles, an appropriate buffer containing a small amount of a blocking agent or a surfactant-containing liquid is used in many cases so that aggregation and the like of the fluorescent dye-containing resin particles can be inhibited as much as possible. For example, Patent Document 1 describes the use of 1% BSA/PBS buffer as a medium for storing fluorescent dye-containing resin particles.

However, even in those cases where such a conventional medium is used, when fluorescent dye-containing resin particles stored for a long period are directly used for various staining processes such as immunostaining, coarse aggregates are generated in the resulting stained cellular tissue image, which may interfere with correctly counting the number of bright spots. In order to avoid such a situation, conventionally, those fluorescent dye-containing resin particles that have been stored in a state of being diluted with a medium over a long time are required to be subjected to pretreatments such as solvent substitution, which is performed by repeating appropriate times the operations of centrifugation, supernatant removal, dilution with a staining solvent and redispersion by ultrasonication, and subsequent filtering treatment, prior to being used for staining; therefore, there is a problem of having to perform complicated operations.

CITATION LIST

Patent Document

Patent Document 1: WO2012/029342

SUMMARY OF THE INVENTION

Problems to be Solved by the Invention

When fluorescent dye-containing resin particles are stored for a long period using a conventional medium, coarse aggregates are often generated upon staining cellular tissues with the stored fluorescent dye-containing resin particles. Such coarse aggregates can usually be observed as aggregates of a size equivalent to a 2.5 to 5-μm square or larger and may reach a size equivalent to a 10-μm square or larger in some cases. It is believed that the fluorescent dye-containing resin particles undergo precipitation and/or aggregation after a long-term storage thereof.

Therefore, an object of the present invention is to provide a medium which is capable of inhibiting precipitation and/or aggregation, particularly aggregation, of fluorescent dye-containing resin particles and enables the fluorescent dye-containing resin particles to be used for staining after a long-term storage without having to perform complicated operations.

Technical Solution

In order to realize at least one of the above-described objects, the present invention provides the following medium:

a medium for storing fluorescent dye-containing resin particles, wherein, in a particle-containing liquid obtained by adding fluorescent dye-containing resin particles to the medium, the rate of change in the backscatter intensity (transmitted light) at the center of the height of the particle-containing liquid left to stand for 24 hours after the addition is not less than −1% based on the particle-containing liquid immediately after the addition.

Advantageous Effects of Invention

By storing fluorescent dye-containing resin particles in the medium of the present invention, cellular tissues can be stained using the fluorescent dye-containing resin particles even after a long-term storage with only a simple operation such as pipetting (stirring), without requiring pretreatments such as solvent substitution, which is performed by repeating appropriate times the operations of centrifugation, supernatant removal, dilution with a staining solvent and redispersion by ultrasonication, and subsequent filtering treatment, before the use for staining as in conventional technologies.

BRIEF DESCRIPTION OF DRAWINGS

FIG. 1 shows the staining result obtained in Example 5 using streptavidin-modified fluorescent dye-containing resin particles immediately after the synthesis thereof.

FIG. 2 shows the staining result obtained in Example 5 using streptavidin-modified fluorescent dye-containing resin particles after one month of storage in the medium of the present invention.

FIG. 3 shows the staining result obtained in Example 11 using streptavidin-modified fluorescent dye-containing resin particles immediately after the synthesis thereof.

FIG. 4 shows the staining result obtained in Example 11 using streptavidin-modified fluorescent dye-containing resin particles after one month of storage in the medium of the present invention.

FIG. 5 shows the staining result obtained in Comparative Example 7 using streptavidin-modified fluorescent dye-containing resin particles immediately after the synthesis thereof.

FIG. 6A shows the staining result obtained in Comparative Example 7 using streptavidin-modified fluorescent dye-containing resin particles after one month of storage in a medium.

FIG. 6B is a sketch illustrating the positions of coarse aggregates in the staining result of Comparative Example 7 shown in FIG. 6A.

FIG. 7 is a chart showing the relationship of the average particle size of the resulting fluorescent dye-containing resin particles with respect to the amount of the added resin material in the production of the fluorescent dye-containing resin particles used in Examples and Comparative Examples.

MODE FOR CARRYING OUT THE INVENTION

The medium according to the present invention will now be described concretely.

[Medium]

The medium according to the present invention is:

a medium for storing fluorescent dye-containing resin particles, wherein, in a particle-containing liquid obtained by adding fluorescent dye-containing resin particles to the medium, the rate of change in the backscatter intensity (transmitted light) at the center of the height of the particle-containing liquid left to stand for 24 hours after the addition is not less than −1% based on the particle-containing liquid immediately after the addition.

That is, when a particle-containing liquid is prepared by adding fluorescent dye-containing resin particles to the medium of the present invention, with the backscatter intensity (transmitted light) measured at the center of the height of the particle-containing liquid immediately after the addition being defined as "$I_0$" and the backscatter intensity (transmitted light) measured at the center of the height of the particle-containing liquid that is left to stand for 24 hours after the addition being defined as "$I_{24}$", the rate of change in the backscatter intensity (transmitted light) at the center of the height of this particle-containing liquid, which is D (%) determined by the following formula:

$$D=(I_{24}-I_0)/I_0\times 100$$

satisfies the relationship of D≥−1. This rate of change, D, represents the degree of aggregation of fluorescent dye-containing resin particles stored in the medium of the present invention and serves as an index for evaluating the performance of the medium in storing fluorescent dye-containing resin particles.

In other words, from a different perspective, whether or not a medium for storing fluorescent dye-containing resin particles corresponds to the medium of the present invention, that is, whether or not a medium for storing fluorescent dye-containing resin particles satisfies the relationship of D≥−1, can be verified by an evaluation method comprising the following steps (1) to (4):

(1) the step of obtaining a particle-containing liquid by adding fluorescent dye-containing resin particles to the medium of interest;

(2) the step of measuring the backscatter intensity (transmitted light) $I_0$ at the center of the height of the particle-containing liquid immediately after the addition;

(3) the step of again measuring the backscatter intensity (transmitted light) $I_{24}$ at the center of the height of the particle-containing liquid after leaving the particle-containing liquid to stand for 24 hours; and (4) the step of determining whether or not the following requirement is satisfied based on the thus measured $I_0$ and $I_{24}$.

$$(I_{24}-I_0)/I_0\times 100\geq -1$$

In the present invention, the "backscatter intensity (transmitted light)", based on which the rate of change (D) is determined, refers to the intensity of a transmitted light or back-scattered light that is generated when a light emitted from a light source travels straight while transmitting or being repeatedly scattered through a sample.

In the present invention, the reason why the backscatter intensity (transmitted light) is measured at the center of the height of a particle-containing liquid in as follows.

In cases where fluorescent dye-containing resin particles to be used for pathological staining are stored in a medium, aggregation of the particles during a long-term storage causes coarse aggregates to be generated when the pathological staining is performed and this interferes with making a correct determination. On the other hand, even if precipitation of the fluorescent dye-containing resin particles occurred during a long-term storage in the medium, by re-dispersing the precipitated particles, the pathological staining can be performed without generation of coarse aggregates. In view of this, for the evaluation of the performance of a medium in storing fluorescent dye-containing resin particles, it is required to be able to observe particle aggregation separately from particle precipitation.

When a particle-containing liquid is left to stand and the particles dispersed therein aggregate, since a change occurs in the amount of the back-scattered light throughout the particle-containing liquid regardless of its height position, the backscatter intensity (transmitted light) at the center of the height is reduced accordingly.

Meanwhile, when the dispersed particles simply precipitate, although the backscatter intensity (transmitted light) at the upper and lower parts of the particle-containing liquid changes with time as the precipitation of the particles proceeds, the backscatter intensity (transmitted light) at the center of the height hardly changes.

Therefore, by setting the position of measuring the backscatter intensity (transmitted light) at the center of the height of a particle-containing liquid, the degree of aggregation of fluorescent dye-containing resin particles in a medium can be properly evaluated, so that the performance of the medium in storing the fluorescent dye-containing resin particles can be appropriately evaluated. In the most ideal mode of the medium of the present invention, no aggregation of fluorescent dye-containing resin particles occurs in the medium even after a long-term storage and, in this case, D=0.

In the present invention, the value of D is prescribed to be not less than −1 because, from the present inventors' experiences, it was considered appropriate to make judgment based on this value when evaluating the performance of a medium in inhibiting the aggregation of fluorescent dye-containing resin particles. This has also be confirmed from its relationship with the evaluation results of immunostaining and morphological staining that were obtained in the below-described Examples and Comparative Examples using fluorescent dye-containing resin particles after one month of storage in a medium. It is noted here that the present inventors presume that the rate of change in the backscatter intensity (transmitted light) at the center of the height of a particle-containing liquid left to stand for one month also has a certain correlation with the value of D.

In the medium of the present invention, the value of D may be larger than 0 (D>0) depending on the measurement conditions; however, such a value of D presents no problem.

In the present invention, the wavelength of the light to be irradiated at the center of the height for the measurement of the backscatter intensity (transmitted light) is not necessarily particularly restricted as long as the backscatter intensity (transmitted light) of the particle-containing liquid of interest can be appropriately measured in relation to fluorescent dye-containing resin particles. However, for an appropriate measurement, it is desired that the wavelength of the irradiated light be longer than the particle size of the fluorescent dye-containing resin particles. Here, a light having a wavelength of about 880 nm is preferably used since it does not require a special measuring instrument.

Further, in the present invention, the measuring instrument used for the evaluation is also not particularly restricted as long as it is capable of appropriately measuring the backscatter intensity (transmitted light) at the center of the height of the particle-containing liquid of interest, and examples of a preferred measuring instrument include TURBISCAN (trademark) manufactured by Formulaction SA. According to this measuring instrument, it is also possible to measure the backscatter intensity (transmitted light) while changing the height position. This is, however, not to forbid use of other spectrophotometer in the measurement of the backscatter intensity (transmitted light).

(Constituents)

In the medium of the present invention, as described above, the rate of change (D (%)) satisfies the specific range prescribed in the present invention. The concrete constitution of the medium of the present invention that satisfies such a rate of change (D (%)) varies depending on the type, the condition of surface modification and the like of the fluorescent dye-containing resin particles to be stored and is thus not uniformly and strictly specified here; however, the medium of the present invention typically comprises a buffer, a protein and a surfactant.

Protein

The protein that can constitute the medium of the present invention is not particularly restricted as long as it does not impair the functions of fluorescent dye-containing resin particles and is capable of inhibiting aggregation of fluorescent dye-containing resin particles. However, when the medium of the present invention is used for storing fluorescent dye-containing resin particles to be used for pathological staining, it is desired that the protein be capable of inhibiting non-specific adsorption to the cellular tissue to be stained. Accordingly, examples of a preferred protein include those proteins that are generally used as a blocking agent, such as BSA and casein.

The content of the protein in the medium of the present invention can be adjusted as appropriate within a range where aggregation of fluorescent dye-containing resin particles can be inhibited; however, it is desired to be, for example, 10% by weight or less (e.g., in a range of 1 to 10% by weight) with respect to the whole medium.

Surfactant

The surfactant that can constitute the medium of the present invention is not particularly restricted as long as it does not impair the functions of fluorescent dye-containing resin particles and is capable of inhibiting aggregation of fluorescent dye-containing resin particles. However, when the medium of the present invention is used for storing fluorescent dye-containing resin particles to be used for pathological staining, there are cases where the fluorescent dye-containing resin particles are directly used for pathological staining in a state of being diluted with the medium of the present invention. In the cellular tissues, parts where the cell nucleus is located are negatively charged because of the phosphate residues constituting the nucleic acid, whereas those parts other than the cell nucleus tend to be positively charged. Therefore, in order to minimize the non-specific adsorption to the cellular tissues, it is desired to use a nonionic surfactant as the surfactant. Particularly, polyoxyethylene sorbitan fatty acid esters such as Tween (registered trademark)-based surfactants can be preferably used and, thereamong, Tween (registered trademark) 20 can be particularly preferably used.

The content of the surfactant in the medium of the present invention can be adjusted as appropriate within a range where aggregation of fluorescent dye-containing resin particles can be inhibited; however, it is desired to be, for example, in a range of 0.1% by weight or less with respect to the whole medium.

Buffer

The buffer that can constitute the medium of the present invention is not particularly restricted as long as it does not impair the functions of fluorescent dye-containing resin particles, and a variety of conventionally known buffers can be used.

In a preferred mode of the present invention, the medium of the present invention is used for storing fluorescent dye-containing resin particles to be used for pathological staining. In this case, as the fluorescent dye-containing resin particles used for pathological staining, the reactive functional group-containing fluorescent dye-containing resin particles described below in the section of "Mode of Fluorescent Dye-containing Resin Particles", particularly those comprising a molecule that is likely to form a bond based on affinity interaction such as biotin, streptavidin and avidin, are often employed. Therefore, it is preferred that the buffer used in the present invention have a pH in a range that does not cause degeneration of such a molecule. Further, in pathological staining with such fluorescent dye-containing resin particles, since the fluorescent dye-containing resin particles may be subjected to the staining in a state of being diluted with the medium of the present invention, it is preferred that the buffer have a pH in a range that is suitable for pathological staining. From these standpoints, the buffer used in the present invention preferably has a pH in a range of 6.0 to 8.0, more preferably in a range of 6.9 to 7.6. Examples of a preferred buffer type include phosphate-buffered physiological saline (PBS), Tris-HCl buffer, phosphate buffer (excluding PBS), and a combination of two or more of these buffers.

Other Components

In the medium of the present invention, in addition to the buffer, protein and surfactant, other component(s) such as a preservative may also be incorporated, as long as the functions of fluorescent dye-containing resin particles are not impaired and aggregation of fluorescent dye-containing resin particles can be inhibited. Examples of the preservative include sodium azide ($NaN_3$).

It is desired that the preservative be incorporated in the buffer at a concentration of 0.015 N or less.

Production Method

The medium of the present invention can be obtained by dissolving the protein and the surfactant as well as the "other component(s)", which is/are optionally added, in the buffer in accordance with a conventional method.

The combination and composition ratio of the constituents, namely the protein and the surfactant, and the "other component(s)" that is/are optionally added vary depending on the type and the like of the fluorescent dye-containing resin particles to be stored and are, therefore, not uniformly and strictly specified here. However, for the adjustment of the combination and composition ratio, reference can be made to the results of the below-described Examples and Comparative Examples.

In the aggregation of fluorescent dye-containing resin particles, it is believed that the electrostatic relation between the fluorescent dye-containing resin particles and/or the electrostatic relation between the medium and the fluorescent dye-containing resin particles are also involved. Accordingly, for the determination of the combination and composition ratio of the constituents, reference can also be made to the zeta potential of the fluorescent dye-containing resin particles in the medium. The zeta potential of the fluorescent dye-containing resin particles can be measured using a common zeta potential-measuring device (such as "Zetasizer Nano" manufactured by Malvern Instruments Ltd.) and adjusted with the protein and preservative as well as, depending on the case, the surfactant. For example, when the medium of the present invention is set to contain a buffer of pH 6.0 to 8.0, the medium of the present invention can be prepared by adjusting the combination and composition ratio of the constituents and/or finely adjusting the pH of the buffer within a range of 6.0 to 8.0 such that the fluorescent dye-containing resin particles have a zeta potential of 0 mV to −10 mV in the resulting medium of the present invention.

(Fluorescent Dye-Containing Resin Particles to be Stored)

The term "fluorescent dye-containing resin particles to be stored" using the medium of the present invention refers to a substance having a structure in which plural fluorescent dye molecules are immobilized in a state of being encapsulated in a resin particle by chemical or physical action, and the form thereof is not particularly restricted.

Examples of the fluorescent dye-containing resin particles of interest in the present invention include conventionally known fluorescent dye-containing resin particles, and their resin may be composed of a thermosetting resin such as a melamine resin or a thermoplastic resin such as a polystyrene resin. However, when the fluorescent dye-containing resin particles are used for pathological staining, clearing with an organic solvent such as xylene may be performed in the process of pathological staining. Therefore, from the standpoint of inhibiting elution of the fluorescent dye in the clearing step using an organic solvent such as xylene, fluorescent dye-containing resin particles whose resin is composed of a thermosetting resin capable of immobilizing a fluorescent dye inside its fine cross-linked structure, such as a melamine resin, are preferred.

The size of the fluorescent dye-containing resin particles is not particularly restricted as long as it is suitable for the intended application such as immunostaining of a tissue section; however, it is usually 10 nm to 500 nm, preferably 40 nm to 200 nm, more preferably 50 nm to 200 nm. Further, the variation coefficient, which represents the variation in the particle size, is also not particularly restricted; however, it is usually 20% or less, preferably 5 to 15%. Fluorescent dye-containing resin particles having such a particle size can be obtained by, for example, the below-described production method.

The size of a fluorescent dye-containing resin particle can be determined by taking an electron micrograph thereof using a scanning electron microscope (SEM), measuring the cross-sectional area of the fluorescent dye-containing resin particle and then determining the particle size as the diameter of a circular area corresponding to the measured value (area-equivalent circle diameter). With regard to the average particle size (average particle diameter) and the variation coefficient of a group of fluorescent dye-containing resin particles, after measuring the particle size (particle diameter) for a sufficient number (for example, 1,000) of the fluorescent dye-containing resin particles in the above-described manner, the average particle size is calculated as the arithmetic mean of the measured values and the variation coefficient is calculated by the following equation: 100×(standard deviation of particle size)/(average particle size).

Fluorescent Dye

The fluorescent dye constituting the fluorescent dye-containing resin particles to which the present invention is applied is not particularly restricted and may be a conventionally known fluorescent dye.

Fluorescent dyes that are generally available or can be prepared may be classified into, for example, rhodamine-based dye molecules, squarylium-based dye molecules, cyanine-based dye molecules, aromatic hydrocarbon-based dye molecules, oxazine-based dye molecules, carbopyronine-based dye molecules, pyrromethene-based dye molecules, Alexa Fluor (registered trademark, manufactured by Invitrogen)-based dye molecules, BODIPY (registered trademark, manufactured by Invitrogen)-based dye molecules, Cy (registered trademark, manufactured by GE Healthcare)-based dye molecules, DY (registered trademark, manufactured by Dyomics GmbH)-based dye molecules, HiLyte (registered trademark, manufactured by AnaSpec Inc.)-based dye molecules, DyLight (registered trademark, manufactured by Thermo Fisher Scientific K.K.)-based dye molecules, ATTO (registered trademark, manufactured by ATTO-TEC GmbH)-based dye molecules, and MFP (registered trademark, manufactured by Mobitec Co., Ltd.)-based dye molecules. The generic names of these dye molecules are designated based on the main structure (skeleton) or registered trademark of the respective compounds; therefore, those of ordinary skill in the art should be able to properly understand the scope of the fluorescent dyes belonging to the respective generic names without having to bear undue trial and error. It is noted here that N,N'-bis (2,6-diisopropylphenyl) -1,6,7,12-tetraphenoxyperylene-3,4:9,10-tetracarboxdiimide used in the below-described Examples corresponds to an aromatic hydrocarbon-based dye molecule.

Further, the fluorescent dye may be subjected to a solubilization treatment for the purposes of, for example, improving the emission intensity of the fluorescent dye and increasing the Stokes shift. This solubilization treatment is not particularly restricted as long as it is a technique capable of solubilizing the fluorescent dye, that is, improving the solubility of the fluorescent dye in water. Specific examples of the solubilization treatment include methods in which a fluorescent dye is treated and allowed to react with an acid (e.g., concentrated sulfuric acid, concentrated hydrochloric acid, acetic acid or formic acid) or an aldehyde (e.g., formaldehyde or acetaldehyde), among which an acid treatment is preferred since it generally shows an excellent effect.

Further, the emission wavelength of the fluorescent dye can be selected as desired in accordance with the intended application. For example, in pathological diagnosis, when such an application where staining with eosin or the like for morphological observation and immunostaining with a fluorescent dye are simultaneously performed is postulated, it is preferred that the fluorescent dye have an emission wavelength in the infrared to near-infrared range so that the light emitted from the fluorescent dye can be visually observed and the emission wavelength of the fluorescent dye does not overlap with that of fluorescence-emitting eosin. For example, a fluorescent dye having its maximum excitation wavelength in a range of 555 to 620 nm and maximum emission wavelength in a range of 580 to 770 nm is preferred.

Resin

The resin constituting the fluorescent dye-containing resin particles to which the present invention is applied may be a thermosetting resin or a thermoplastic resin. For example, from the standpoint of inhibiting elution of the fluorescent dye in the clearing step using an organic solvent such as xylene, a resin comprising a thermosetting resin such as a melamine resin, which is capable of immobilizing the fluorescent dye inside its fine cross-linked structure, is preferred. In a preferred mode of the present invention, the resin constituting the fluorescent dye-containing resin particles to which the present invention is applied is a thermosetting resin, more specifically a resin consisting of only a thermosetting resin such as a melamine resin.

Examples of the thermosetting resin include those which contain a structural unit formed from at least one monomer selected from the group consisting of melamine, urea, guanamines (including benzoguanamine, acetoguanamine and the like), phenols (including phenol, cresol, xylenol and the like), xylene and derivatives thereof. Any one of these monomers may be used individually, or two or more thereof may be used in combination. If desired, one or more co-monomers other than the compounds may also be used in combination.

Specific examples of the thermosetting resin include melamine-formaldehyde resins, urea-formaldehyde resins, benzoguanamine-formaldehyde resins, phenol-formaldehyde resins and metaxylene-formaldehyde resins.

As a starting material of these thermosetting resins, in addition to the above-described monomers per se, a prepolymer obtained by allowing such a monomer to react with formaldehyde and other compound such as a cross-linking agent in advance can also be used. For example, in the production of a melamine-formaldehyde resin, generally, methylol melamine prepared by condensation between melamine and formaldehyde under an alkaline condition is used as a prepolymer, and this compound may further be subjected to alkyl-etherification. Examples of the alkyl-etherification of methylol melamine include methylation for improvement of the stability in water, and butylation for improvement of the solubility in an organic solvent.

Further, in the thermosetting resin, at least some of the hydrogens contained in the structural unit may be substituted with a charged substituent or a substituent capable of forming a covalent bond. Such a thermosetting resin can be synthesized by using, as a starting material, a monomer in which at least one hydrogen is substituted with the substituent (derivatized monomer) by a known method. Normally, melamine resins, urea resins, benzoguanamine resins and the like naturally contain an amino group or a cation generated from a moiety originated from an amino group, and phenol resins, xylene resins and the like naturally contain a hydroxyl group or an anion generated from a moiety originated from a hydroxyl group.

Such a thermosetting resin can be synthesized in accordance with a known method. For example, a melamine-formaldehyde resin can be synthesized by heating and polycondensing methylol melamine prepared in advance in the above-described manner, with an addition of, as required, a reaction accelerator such as an acid.

Meanwhile, examples of the thermoplastic resin include those which contain a structural unit formed from at least one monofunctional monomer selected from the group consisting of styrene, (meth)acrylic acid, alkyl esters thereof, acrylonitrile and derivatives thereof (a monomer having one group involved in polymerization reaction in one molecule, which group is a vinyl group in the above-described case). Any one of these monomers may be used individually, or two or more thereof may be used in combination. If desired, one or more co-monomers other than the compounds may also be used in combination.

Specific examples of the thermoplastic resin include polystyrenes, styrene-based resins composed of styrene and other monomer(s), polymethyl methacrylates, acrylic resins composed of (meth) acrylic acid, an alkyl ester thereof and other monomer(s), polyacrylonitriles, AS resins (acrylonitrile-styrene copolymers) and ASA resins (acrylonitrile-styrene-methyl acrylate copolymers), and acrylonitrile-based resins composed of acrylonitrile and other monomer(s).

The thermoplastic resin may also contain, for example, a structural unit formed from a polyfunctional monomer such as divinylbenzene (a monomer having two or more groups involved in polymerization reaction in one molecule, which groups are vinyl groups in the above-described case), that is, a cross-linked moiety. Examples of such a thermoplastic resin include cross-linked polymethyl methacrylates.

In the thermoplastic resin, at least some of the hydrogens contained in the structural unit may be substituted with a charged substituent or a substituent capable of forming a covalent bond. Such a thermoplastic resin can be synthesized by using, as a starting material, a monomer in which at least one hydrogen is substituted with the substituent (derivatized monomer), such as 4-aminostyrene.

Further, the thermoplastic resin may also contain a structural unit comprising a functional group used for surface modification of the resulting fluorescent dye-containing resin particles. For example, by using an epoxy group-containing monomer such as glycidyl methacrylate as a starting material, fluorescent dye-containing resin particles on which epoxy groups are oriented on the surface can be prepared. These epoxy groups can be converted into amino groups by allowing them to react with an excess amount of aqueous ammonia. In the thus formed amino groups, various biomolecules can be incorporated in accordance with a known method. As required, the incorporation of various biomolecules into the amino groups can be carried out through molecules that serve as linkers.

Mode of Fluorescent Dye-Containing Resin Particles

The fluorescent dye-containing resin particles to which the present invention is applied comprise the fluorescent dye and resin and may be subjected to surface modification.

The medium of the present invention can be particularly preferably used for storing fluorescent dye-containing resin particles that are used for pathological staining such as immunostaining. It is preferred that the fluorescent dye-containing resin particles to which the present invention is applied further comprise a reactive functional group so that the fluorescent dye-containing resin particles are easily bound with a molecule-recognizing substance (e.g., an antibody) capable of recognizing a biological substance to be detected by pathological staining (more specifically, a biological substance that can be an antigen). Examples of the reactive functional group include chemical functional groups, such as a carboxyl group, an amino group, an aldehyde group, a thiol group and a maleimide group; and molecules that are likely to form a bond based on affinity interaction, such as biotin, streptavidin and avidin. In the fluorescent dye-containing resin particles, a linker or spacer having an appropriate chain length may exist between the main part of the fluorescent dye-containing resin particles (that is, the part of the fluorescent dye-containing resin particles that excludes the reactive functional group and optional linker or spacer).

Method of Producing Fluorescent Dye-Containing Resin Particles

The fluorescent dye-containing resin particles to which the present invention is applied can be produced in accordance with a polymerization step known for various resins.

Fluorescent dye-containing resin particles whose resin is composed of a thermosetting resin can be produced in accordance with a known emulsion polymerization method. For example, the polymerization step of the fluorescent dye-containing resin particles whose resin is composed of a thermosetting resin may be a step of generating fluorescent dye-encapsulating resin particles by heating a reaction mixture which contains a fluorescent dye and a resin material (a monomer, an oligomer or a prepolymer), and preferably an appropriate known surfactant and an appropriate known polymerization reaction accelerator, and thereby allowing polymerization reaction of the resin to proceed. In this case, the order of adding the components contained in the reaction mixture is not particularly restricted.

The conditions of the polymerization reaction (e.g., temperature and time) can be set as appropriate taking into consideration the type of the resin, the composition of the material mixture and the like. For the synthesis of a thermosetting resin such as a melamine resin, the reaction temperature is usually 70 to 200° C. and the reaction time is usually 20 to 120 minutes. Here, it is appropriate that the reaction temperature be a temperature at which the performance of the fluorescent dye is not reduced (within the range of the heat resistant temperature). The heating can be performed in a plurality of steps and, for example, the material mixture may first be allowed to react for a certain time at a relatively low temperature and then heated and allowed to further react for a certain time at a relatively high temperature. After the completion of the polymerization reaction, impurities such as unreacted resin material, fluorescent dye and surfactant are removed, and the thus generated fluorescent dye-containing resin particles can be recovered and purified.

Further, in the production of fluorescent dye-containing resin particles whose resin is composed of a thermosetting resin, after the polymerization step, as required depending on the intended application of the fluorescent dye-containing resin particles, a modification step can also be performed as a step of introducing the reactive functional group described above in the section of "Mode of Fluorescent Dye-containing Resin Particles" to the surface of the fluorescent dye-containing resin particles. The introduction of the reactive functional group can be appropriately performed by a conventional method.

Meanwhile, fluorescent dye-containing resin particles whose resin is composed of a thermoplastic resin can be produced in the same manner as the fluorescent dye-containing resin particles whose resin is composed of a thermosetting resin, except that, as a polymerization step, a step of generating fluorescent dye-encapsulating resin particles by heating a reaction mixture which contains a fluorescent dye, a resin material and a polymerization initiator (e.g., benzoyl peroxide or azobis-isobutyronitrile) and thereby allowing polymerization reaction of the resin to proceed is performed in accordance with a conventional method.

(Application)

The above-described medium of the present invention can be suitably used for storing fluorescent dye-containing resin particles, particularly fluorescent dye-containing resin particles used for pathological staining. From a different perspective, the method of storing fluorescent dye-containing resin particles can be seen as a method which comprises adding the fluorescent dye-containing resin particles to the medium of the present invention. The fluorescent dye-containing resin particles can be stored usually under refrigeration (for example, at 4 to 5° C.).

Specific examples of the pathological staining include immunostaining.

EXAMPLES

Examples and Comparative Examples according to the present invention will now be described referring to the drawings.

The fluorescent dye-containing resin particles of Examples and Comparative Examples were measured or evaluated by the following methods.

(Method of Measuring Average Particle Size of Fluorescent Dye-Containing Resin Particles)

A photograph of the fluorescent dye-containing resin particles of interest was taken under a scanning electron microscope (SEM), the cross-sectional area was measured for a sufficient number of particles, and the particle size was determined as the diameter of a circular area corresponding to the respective measured values. In the below-described Synthesis Examples, the arithmetic mean of the particle sizes of 1,000 particles was defined as the average particle size.

Synthesis Examples 1-1 to 1-7: Preparation of Fluorescent Dye-Containing Resin Particles As fluorescent dye-containing resin particles of Synthesis Examples 1-1 to 1-7, using a conventionally known method, fluorescent dye-containing resin particles A1 to A7 having an average particle size of 40, 60, 80, 100, 150, 200 and 250 nm, respectively, were each prepared.

As an example of the method of producing the fluorescent dye-containing resin particles, the method of producing the fluorescent dye-containing resin particles A5 is described below.

Synthesis Example 1-5

By treating N,N'-bis (2,6-diisopropylphenyl)-1,6,7,12-tetraphenoxyperylene-3,4:9,10-tetracarboxdiimide with concentrated sulfuric acid, a sulfo group was introduced to give a corresponding sulfonic acid. This sulfonic acid was converted into a corresponding acid chloride by a conventional method.

After adding 14.4 mg of the thus obtained acid chloride to 22.5 mL of water, the resultant was heated at 70° C. for 20 minutes on a hot stirrer and 0.65 g of a melamine resin Nikalac MX-035 (manufactured by Nippon Carbide Industries Co., Ltd.) was added thereto, followed by heating of the resulting mixture with stirring for another 5 minutes. Then, 100 μL of formic acid was further added, and the resultant was heated with stirring at 60° C. for 20 minutes and subsequently cooled to room temperature. Thereafter, the resulting reaction mixture was placed in a centrifugal tube and centrifuged at 12,000 rpm for 20 minutes, followed by removal of the resulting supernatant. The precipitates were washed with ethanol and water.

Then, 0.1 mg of the thus obtained particles was dispersed in 1.5 mL of EtOH (ethanol), and 2 μL of aminopropyltrimethoxysilane LS-3150 (manufactured by Shin-Etsu Chemical Co., Ltd.) was added thereto. The resultant was allowed to react for 8 hours so as to perform a surface amination treatment.

The thus obtained dye-containing nanoparticles were adjusted with PBS (phosphate-buffered physiological saline) containing 2 mM of EDTA (ethylenediamine tetraacetic acid) to a concentration of 3 nM, and this solution was mixed with SM (PEG) 12 (manufactured by Thermo Fisher Scientific K.K.; succinimidyl-[N-maleimidopropionamido)-dodecaethylene glycol]ester) to a final concentration of 10 mM and allowed to react for 1 hour. The thus obtained mixture was centrifuged at 10,000 G for 20 minutes, and the resulting supernatant was removed. Then, PBS containing 2 mM of EDTA was added to disperse the precipitates, and the resulting dispersion was centrifuged again. The precipitates were washed three times by the same procedure to give fluorescent dye-containing resin particles (fluorescent particles) A5 having a maleimide group at a terminal.

When the particle size was measured for the thus obtained fluorescent dye-containing resin particles A5 under an electron microscope by the above-described method, the average particle size was found to be 150 nm.

Synthesis Examples 1-1 to 1-4, 1-6 and 1-7

Fluorescent dye-containing resin particles A1 to A4, A6 and A7 of Synthesis Examples 1-1 to 1-4, 1-6 and 1-7, which had different particle sizes from the fluorescent dye-containing resin particles A5 of Synthesis Example 1-5, were also each synthesized in the same manner as in Synthesis Example 1-5, except that the amount of the resin was changed as appropriate while maintaining the dye/added resin amount in the synthesis constant.

For reference, FIG. 7 shows the relationship of the average particle size of the resulting fluorescent dye-containing resin particles with respect to the amount of the added resin material (the melamine resin in Synthesis Examples 1-1 to 1-7) in a case where fluorescent dye-containing resin particles are synthesized under the same conditions as in Synthesis Example 1-5.

It is noted here that, in the following descriptions, in order to distinguish the fluorescent dye-containing resin particles A1 to A7 from the below-described streptavidin-modified fluorescent dye-containing resin particles, the fluorescent dye-containing resin particles A1 to A7 may be referred to as "maleimide group-modified fluorescent dye-containing resin particles A1 to A7", respectively, and these resin particles may be collectively referred to as "maleimide group-modified fluorescent dye-containing resin particles".

Synthesis Examples 2-1 to 2-7: Synthesis of Streptavidin-Modified Fluorescent Dye-Containing Resin Particles The maleimide group-modified fluorescent dye-containing resin particles A1 to A7 were each modified with streptavidin in the below-described manner to give streptavidin-modified fluorescent dye-containing resin particles S1 to S7, respectively.

A thiol group addition treatment was performed for streptavidin (manufactured by Wako Pure Chemical Industries, Ltd.), by allowing the streptavidin to react with N-succinimidyl-S-acetylthioacetate (SATA), and then subjecting the resultant to a known hydroxylamine treatment for deprotection of S-acetyl group. Then, by filtering the resultant through a gel filtration column, a solution of streptavidin capable of binding to fluorescent dye-containing resin particles was obtained.

The thus obtained streptavidin solution was mixed with 1 mL of a liquid containing fluorescent dye-containing resin particles which was obtained by diluting the maleimide group-modified fluorescent dye-containing resin particles with PBS containing 2 mM of EDTA to a concentration of 1 nM, and the resulting mixture was allowed to react at room temperature for 1 hour, whereby the fluorescent dye-containing resin particles were bound with streptavidin. The resultant was then centrifuged and washed with PBS containing 2 mM of EDTA, and only streptavidin-modified fluorescent dye-containing resin particles were recovered.

The thus obtained streptavidin-modified fluorescent dye-containing resin particles were subjected to various evaluations in a state of being once diluted with 1% BSA-containing PBS buffer.

Examples 1 to 12 and Comparative Examples 1 to 16

(Medium and Fluorescent Dye-Containing Resin Particles)

As a medium, a Tris buffer containing 0.6% α-casein, 0.6% β-casein, 3% BSA, 0.1% Tween (registered trademark) 20 and 0.015 N $NaN_3$ (pH=6.9) was employed in Examples 1 to 6 and Comparative Example 1; a PBS buffer containing 10% BSA, 0.1% Tween (registered trademark) 20 and 0.05 N $NaN_3$ (pH=7.6) was employed in Examples 7 to 12 and Comparative Example 2; a PBS buffer containing 1% BSA (pH=7.2) was employed in Comparative Examples 3 to 9; and a polymeric surfactant (0.1% DISPERBYK-194: pH=7.0) was employed in Comparative Examples 10 to 16.

Further, in Examples and Comparative Examples, as fluorescent dye-containing resin particles, the streptavidin-modified fluorescent dye-containing resin particles S1 to S7 were each used as shown in Table 1 below.

The fluorescent dye-containing resin particles were subjected to the following storage and evaluations using the medium.

(Storage of Fluorescent Dye-Containing Resin Particles)

The respective streptavidin-modified fluorescent dye-containing resin particles contained in a 1% BSA/PBS solution were subjected to removal of supernatant, substitution with the medium and then a filtering treatment (0.65 μm, manufactured by Merck Millipore Corporation). Thereafter, the resultant was adjusted by dilution with the medium to an intended concentration of the streptavidin-modified fluorescent dye-containing resin particles (0.2 nM), thereby giving a medium containing the respective fluorescent dye-containing resin particles.

The fluorescent dye-containing resin particles were stored in this form of being contained in the medium in a refrigerator at 4° C.

(Evaluation of Precipitation and Aggregation of Fluorescent Dye-Containing Resin Particles)

Precipitation and aggregation of fluorescent dye-containing resin particles were evaluated using TURBISCAN (trademark) (TURBISCAN Lab) manufactured by Formulaction SA.

Specifically, for the respective streptavidin-modified fluorescent dye-containing resin particles of immediately after the synthesis, a medium containing the fluorescent dye-containing resin particles was prepared in accordance with the method described above in the section of "Storage of Fluorescent Dye-containing Resin Particles" and, for this medium containing the fluorescent dye-containing resin particles, the backscatter intensity (transmitted light) was measured by TURBISCAN using a light source emitting an infrared radiation of 880 nm in wavelength. The measurement was continued for 24 hours while sampling at 30-minute intervals.

With the backscatter intensity (transmitted light) measured at the center of the height immediately after the start of the measurement (which corresponds to the "backscatter intensity (transmitted light) measured at the center of the height . . . immediately after the addition") being defined as "$I'_0$" and the backscatter intensity (transmitted light) measured at the center of the height after allowing the medium containing the fluorescent dye-containing resin particles to stand for 24 hours after the start of the measurement being defined as "$I'_{24}$", the rate of change in the backscatter intensity (transmitted light) at the center of the height, D' (%), was calculated as follows.

$$D'=(I'_{24}-I'_0)/I'_0\times 100$$

Table 1 shows the rate of change (D') determined for the respective Examples and Comparative Examples. For example, in Example 5, based on the start of the measurement, the backscatter intensity (transmitted light) showed a −0.9% change at 24 hours after the start of the measurement.

(Staining with Fluorescent Dye-Containing Resin Particles)

In order to evaluate the performance of each medium, using the respective streptavidin-modified fluorescent dye-containing resin particles immediately after the synthesis and after one month of storage in the medium, the following immunostaining, morphological staining and observation were performed.

As a tissue cell slide, a breast cancer tissue array manufactured by US Biomax, Inc. (model: BR243 Series (24-core); core diameter=1.5 mm) was employed.

Immunostaining

The tissue cell slide was deparaffinized in accordance with a conventional method and then washed by substitution with water. The thus washed tissue cell slide was subjected to a 5-minute autoclave treatment at 121° C. in 10 mM citrate buffer (pH 6.0), thereby performing an antigen activation treatment.

After the activation treatment, the tissue cell slide was washed with PBS buffer and then subjected to a 1-hour blocking treatment with 1% BSA-containing PBS buffer in a moist chamber.

After the blocking treatment, an anti-HER2 rabbit monoclonal antibody (4B5, manufactured by Ventana Medical Systems, Inc.) diluted with 1% BSA-containing PBS buffer to a concentration of 0.05 nM was allowed to react with the tissue cell slide for 2 hours. After washing this tissue cell slide with PBS buffer, the tissue cell slide was further allowed to react for 30 minutes with a biotin-labeled anti-rabbit monoclonal antibody that would bind to 4B5 and had been diluted with 1% BSA-containing PBS buffer to a concentration of 2 μg/mL.

After the reaction with the biotin-labeled anti-rabbit monoclonal antibody, the tissue cell slide was stained with the fluorescent dye-containing resin particles of interest.

It is noted here that, for staining with the fluorescent dye-containing resin particles immediately after the synthesis thereof, the tissue cell slide was allowed to react for 3 hours with the fluorescent dye-containing resin particles of immediately after the synthesis that had been diluted with 1% BSA-containing PBS buffer to a concentration of 0.2 nM, in a neutral pH environment (pH 6.9 to 7.4) at room temperature. Prior to the dilution of the fluorescent dye-containing resin particles to a concentration of 0.2 nM, the solvent was substituted with the medium by repeating appropriate times the operations of centrifugation, removal of supernatant, dilution with the medium and redispersion by ultrasonication, and the resultant was subsequently subjected to a filtering treatment (0.65 μm, manufactured by Merck Millipore Corporation).

Meanwhile, staining with the fluorescent dye-containing resin particles after one month of storage in the medium was also performed in the same manner, except that the fluorescent dye-containing resin particles that had been stored for one month in the medium were used in place of the fluorescent dye-containing resin particles of immediately after the synthesis that were diluted to 0.2 nM. In this case, the fluorescent dye-containing resin particles that had been stored in the form of the above-described medium containing the fluorescent dye-containing resin particles were subjected to pipetting (stirring) and then directly used for staining without being diluted. In Examples 1 and 7, however, the fluorescent dye-containing resin particles were directly used for staining without being subjected to pipetting since no precipitation thereof was observed. In the present specification, unless otherwise specified, the term "pipetting" means stirring of a liquid of interest that is performed by repeating the operations of sucking up and discharging the liquid using a pipette.

In any of the above-described cases, after the reaction with the fluorescent dye-containing resin particles, the tissue cell slide was washed with PBS buffer.

Morphological Staining

The tissue cell slides subjected to the immunostaining were each further subjected to morphological staining.

Specifically, the immunostained tissue cell slide was subjected to hematoxylin staining (HE staining) for 1 minute using Mayer's hematoxylin solution. Then, the tissue cell slide was washed with running water of about 45° C. for 3 minutes. Next, an operation of immersing the tissue cell slide in pure ethanol for 5 minutes was repeated four times to perform washing and dehydration. Subsequently, an operation of immersing the tissue cell slide in xylene for 5 minutes was repeated four times to perform clearing. Lastly, the tissue section was mounted with a mounting medium ("Entellan New", manufactured by Merck KGaA) to give a sample slide for observation.

Observation

The tissue section on the sample slide that had been subjected to the immunostaining and morphological staining was allowed to emit fluorescence by irradiating thereto a prescribed excitation light. The tissue section in this state was observed and photographed under a fluorescence microscope (BX-53, manufactured by Olympus Corporation). It is noted here that the observation and photographing were performed in 10 visual fields for each core (a single tissue spot) on the sample slide. In this process, an objective lens of ×40 magnification and an ocular lens of ×10 magnification were used. Further, the bright spots were measured by ImageJ FindMaxima method.

The excitation light was set to have a wavelength of 575 to 600 nm through an optical filter. In addition, the wavelength range (nm) of the fluorescence to be observed was also set at 612 to 682 nm through an optical filter.

The conditions of the excitation wavelength in the microscope observation and image acquisition were set such that the intensity of the irradiation light in the vicinity of the center of the visual field was 900 $W/cm^2$ for excitation at 580 nm. In the image acquisition process, a photograph was taken by arbitrarily setting the exposure time such that the image brightness was not saturated (for example, the exposure time was set at 4,000 μs).

The evaluation results are shown in Table 1 below. For reference, FIGS. 1, 3 and 5 show the stained images obtained using the fluorescent dye-containing resin particles immediately after the synthesis in Examples 5 and 11 and Comparative Example 7, respectively; and FIGS. 2, 4 and 6A show the stained images obtained using the fluorescent dye-containing resin particles after one month of storage in Examples 5 and 11 and Comparative Example 7, respectively.

As for the determination of the presence or absence of coarse aggregates, an evaluation of "x" (presence of coarse aggregates) was given when about 10 visual fields were observed for each tissue cell slide and three or more aggregates having an apparent size of 1 to 2-mm square (that is, an actual size equivalent to 2.5 to 5-μm square) or larger were observed under a microscope. For example, in the case of Comparative Example 7, on the stained image shown in FIG. 6A which was obtained using the fluorescent dye-containing resin particles after one month of storage, three coarse aggregates were confirmed as illustrated in the sketch of FIG. 6B.

adding the fluorescent dye-containing resin particles in a liquid comprising a buffer, a protein, and a surfactant, thereby obtaining a particle-containing liquid, wherein said fluorescent dye-containing resin particles have an average particle size of 40 nm to 200 nm, and wherein the rate of change in the backscatter intensity (transmitted light) at the center of the height of said particle-containing liquid left to stand for 24 hours after said adding is not less than −1% based on said particle-containing liquid immediately after said adding.

2. The method according to claim 1 wherein said surfactant is a nonionic surfactant.

3. The method according to claim 1, wherein the wavelength of a light irradiated at said center of said height is longer than the particle size of said fluorescent dye-containing resin particles.

4. The method according to claim 1, wherein said fluorescent dye-containing resin particles are capable of being used for pathological staining.

5. The method according to claim 1, wherein said fluorescent dye-containing resin particles further comprise a reactive functional group.

TABLE 1

| | Used fluorescent dye-containing resin particle | | Staining results immediately | Evaluation of storage performance | | | | |
|---|---|---|---|---|---|---|---|---|
| | | | | | After 24 hours Rate of change in the backscatter intensity | After one month of storage | | |
| | Type | Particle size (nm) | after synthesis† | Composition of medium | (transmitted light) at the center of the height, D' (%) | Staining results‡ | Pre-staining operation | Note |
| Example 1 | S1 | 40 | ○ | (0.6% α-casein + | −0.1 | ○ | none | |
| Example 2 | S2 | 60 | ○ | 0.6% β-casein + | −0.2 | ○ | pipetting | |
| Example 3 | S3 | 80 | ○ | 3% BSA + 0.1% | −0.4 | ○ | pipetting | |
| Example 4 | S4 | 100 | ○ | Tween 20 + 0.015N | −0.8 | ○ | pipetting | |
| Example 5 | S5 | 150 | ○ | $NaN_3$)/Tris buffer | −0.9 | ○ | pipetting | |
| Example 6 | S6 | 200 | ○ | | −1 | ○ | pipetting | |
| Comparative Example 1 | S7 | 250 | x | | −2 | x | pipetting | *1 |
| Example 7 | S1 | 40 | ○ | (10% BSA + 0.1% | 0 | ○ | none | |
| Example 8 | S2 | 60 | ○ | Tween 20 + 0.05N | 0.1 | ○ | pipetting | |
| Example 9 | S3 | 80 | ○ | $NaN_3$)/PBS buffer | 0.3 | ○ | pipetting | |
| Example 10 | S4 | 100 | ○ | | 0.5 | ○ | pipetting | |
| Example 11 | S5 | 150 | ○ | | 0.8 | ○ | pipetting | |
| Example 12 | S6 | 200 | ○ | | −0.9 | ○ | pipetting | |
| Comparative Example 2 | S7 | 250 | ○ | | −2.4 | x | pipetting | *1 |
| Comparative Example 3 | S1 | 40 | ○ | 1% BSA/PBS (prior | −1.2 | Δ | pipetting | *1 |
| Comparative Example 4 | S2 | 60 | ○ | art) | −1.4 | Δ | pipetting | *1 |
| Comparative Example 5 | S3 | 80 | ○ | | −1.8 | Δ | pipetting | *1 |
| Comparative Example 6 | S4 | 100 | ○ | | −2.4 | Δ | pipetting | *1 |
| Comparative Example 7 | S5 | 150 | ○ | | −2.6 | Δ | pipetting | *1 |
| Comparative Example 8 | S6 | 200 | ○ | | −3.2 | Δ | pipetting | *1 |
| Comparative Example 9 | S7 | 250 | x | | −4.1 | xx | pipetting | *2 |
| Comparative Example 10 | S1 | 40 | x | Polymeric | −1.3 | xx | pipetting | *2 |
| Comparative Example 11 | S2 | 60 | x | surfactant | −1.5 | xx | pipetting | *2 |
| Comparative Example 12 | S3 | 80 | x | (0.1% | −1.9 | xx | pipetting | *2 |
| Comparative Example 13 | S4 | 100 | x | DISPERBYK-194) | −2.4 | xx | pipetting | *2 |
| Comparative Example 14 | S5 | 150 | x | | −2.8 | xx | pipetting | *2 |
| Comparative Example 15 | S6 | 200 | x | | −3.5 | xx | pipetting | *2 |
| Comparative Example 16 | S7 | 250 | x | | −5.5 | xx | pipetting | *2 |

<†Evaluation of staining immediately after synthesis>

○: The tissue cell slide was stained.

x: The tissue cell slide could not be stained.

<‡Evaluation of staining after one month of storage>

○: In comparison to the staining performed immediately after the synthesis, 80% of the bright spots were maintained.

Δ: At least 80% of the bright spots were maintained; however, coarse aggregates were observed.

x: Not more than 80% of the bright spots were maintained and coarse aggregates were observed.

xx: The tissue cell slide could not be stained and coarse aggregates were observed.

<Note>

*1: Stainable even after one month when ultrasonication, solvent substitution and filtering treatment were performed prior to the staining.

*2: Not stainable even when ultrasonication, solvent substitution and filtering treatment were performed prior to the staining.

The invention claimed is:

1. A method of storing fluorescent dye-containing resin particles comprising

6. The method according to claim 1, wherein a resin constituting said fluorescent dye-containing resin particles is a thermosetting resin.

7. The method according to claim 1, wherein the protein is casein.

8. The method according to claim 1, wherein the protein comprises 0.6% by weight of α-casein, 0.6% by weight of β-casein, and 3% by weight of bovine serum albumin (BSA), based on the liquid comprising a buffer, a protein, and a surfactant.

9. The method according to claim 1, wherein the protein comprises 10% by weight of bovine serum albumin (BSA), based on the liquid comprising a buffer, a protein, and a surfactant.

10. The method according to claim 1, wherein the buffer is at least one of a tris-HCl buffer and a phosphate buffer that is not phosphate-buffered saline (PBS).

11. The method according to claim 1, wherein the liquid further comprises a preservative.

12. The method according to preservative is sodium azide ($NaN3$).

13. The method according to claim 11, wherein the preservative is incorporated in the buffer at a concentration of 0.015 N or less.

* * * * *